United States Patent [19]

Dillon

[11] Patent Number: 4,832,009

[45] Date of Patent: May 23, 1989

[54] SEMI-INTERPENETRATING NETWORK POLYMER BACKSHEET BANDAGE

[75] Inventor: Mark E. Dillon, Southampton, Pa.

[73] Assignee: Bio Med Sciences, Inc., Amherst, N.Y.

[21] Appl. No.: 137,418

[22] Filed: Dec. 23, 1987

[51] Int. Cl.$^4$ ............................................. A61L 15/00
[52] U.S. Cl. .................................... 128/156; 128/155; 604/304; 428/172; 523/111; 424/447
[58] Field of Search ............... 128/155, 156, DIG. 21; 604/304, 307; 106/176; 428/172; 523/111; 424/443, 447

[56] References Cited

U.S. PATENT DOCUMENTS

| | | |
|---|---|---|
| 3,315,020 | 4/1967 | Gore. |
| 3,715,334 | 2/1973 | Karsteat. |
| 3,775,452 | 11/1973 | Karsteat. |
| 3,814,730 | 6/1974 | Karsteat. |
| 3,997,702 | 12/1976 | Schurb et al. ........................ 428/352 |
| 4,043,331 | 8/1977 | Martin et al. ........................ 128/156 |
| 4,096,227 | 6/1978 | Gore ................................ 264/210 R |
| 4,187,390 | 2/1980 | Gore. |
| 4,194,040 | 3/1980 | Breton et al. ........................ 428/308 |
| 4,194,041 | 3/1980 | Gore et al. ........................ 428/315 |
| 4,202,331 | 5/1980 | Yale ................................. 128/1 R |
| 4,297,265 | 10/1981 | Olsen .......................... 260/33.6 SB |
| 4,300,532 | 11/1981 | Olsen .................................. 126/417 |
| 4,360,015 | 11/1982 | Mayer ................................ 128/156 |
| 4,373,519 | 2/1983 | Errede et al. ........................ 128/156 |
| 4,460,642 | 7/1984 | Errede et al. ........................ 128/156 |
| 4,545,372 | 10/1985 | Lauritzen ............................ 128/156 |
| 4,600,001 | 7/1986 | Gilman ............................... 128/156 |
| 4,613,544 | 9/1986 | Burleigh .......................... 428/315.5 |
| 4,664,662 | 5/1987 | Webster ............................. 604/369 |
| 4,764,560 | 8/1988 | Mitchell ............................ 525/104 |

FOREIGN PATENT DOCUMENTS 0837377 6/1960 United Kingdom ............... 128/156

OTHER PUBLICATIONS

Sperling, *Interpenetrating Polymer Networks and Related Materials*, Plenum Press, New York, 1981, pp. 1–5.

Primary Examiner—Richard J. Apley
Assistant Examiner—Paul Prebilic

[57] ABSTRACT

An improved bandage comprises a backing sheet constructed of a semi-interpenetrating polymer network. Use of a semi-interpenetrating polymer network allows for an extremely desirable combination of gas permeability and hydrostatic resistance. This construction of backing sheet provides for suitable vapor permeability and sufficient water impermeability because the pores therein are of a colloidal size range and the surface tension thereof results in the backing material being hydrophobic.

13 Claims, 1 Drawing Sheet

SEMI-INTERPENETRATING NETWORK POLYMER BACKSHEET BANDAGE

BACKGROUND OF THE INVENTION

This invention relates to bandages and bandage materials. More particularly, this invention relates to self adhesive, air permeable, water impermeable bandages.

Self-adhesive wound dressings or bandages are generally composed of a backing sheet, an absorbent material, and an adhesive material. The backing sheet serves as a protective barrier preventing mechanical and foreign particle irritation of the wound or other area of the skin adversely affected by injury, disease or the like. The backing sheet further serves as a mechanical support for the absorbent material. Finally, ideally the backing sheet does not inhibit healing by preventing air flow to and from the wound. The ingress and egress of air from the site hinders the creation of a stagnant healing atmosphere which would result in a localized unsanitary condition. This last function is often at odds with the first two functions mentioned because in order to have adequate mechanical support and protective coverage, prior art devices are constructed in a manner which inhibits air permeability. In the alternative, air flow is emphasized to the detriment of protective action and mechanical support. This is seen in the well known prior art wherein the backing material is perforated to achieve gas flow, yet only limited hydrostatic resistance is offered.

The absorbent material in prior art bandages serves to absorb wound discharge. The fastening means is usually adhesive and it serves to retain the bandage at the application site or wound. Note that the absorbent material is not necessary for all applications of bandaging material. For example, in a situation where visual inspection of a wound is important and bodily fluids are not secreted to the extent that an absorbent gauze is necessary, a transparent membrane having the feature of gas permeability and yet offering adequate protection of the wound site is desirable.

SUMMARY OF THE INVENTION

The bandage of the present invention utilizes a backing sheet comprising a semi-interpenetrating polymer network of fibrillated polytetrafluoroethylene and crosslinked polyorganosiloxane as described in United States patent application Ser. No. 000,389, which disclosure is incorporated herein by reference. The polytetrafluoroethylene (PTFE) material and the polyorganosiloxane form a porous membrane. This construction of backing sheet provides for suitable vapor permeability and sufficient water impermeability because the pores therein are of a colloidal size range and the surface tension thereof results in the backing material being hydrophobic. Furthermore, the backing sheet is transparent or translucent and waterproof up to pressures of about 200 psi, although most uses will probably require a resistance to a water pressure differential, as measured across the backing material, of no greater than about 10 psi.

When the backing is coated on one side with a fastening means such as pressure sensitive adhesive, and when an absorbent material such as gauze is fastened to the fastening material, the resulting bandage provides a waterproof yet breathable article well suited to the healing of wound sites. Note that the pressure sensitive adhesive is preferably of a type selected so as to not substantially interfere with the breathability characteristics of the backing material. Alternatively, a strengthening or reinforcing means such as a woven or nonwoven scrim can be applied to a surface of the backing sheet to reinforce the bandage. This provides a bandage suitable for use where higher tensile strengths are desired, and yet still provides a gas permeable, water impermeable bandage.

It is an object of this invention to provide a unique construction for a bandage.

A further object of the invention is to achieve a bandage with a backing sheet that achieves a novel balance between gas permeability and mechanical support for the absorbant material.

It is a further object of the invention to utilize semi-interpenetrating polymer networks in bandaging material.

DETAILED DESCRIPTION OF THE PREFERRED EMBODIMENT

Figure 1:
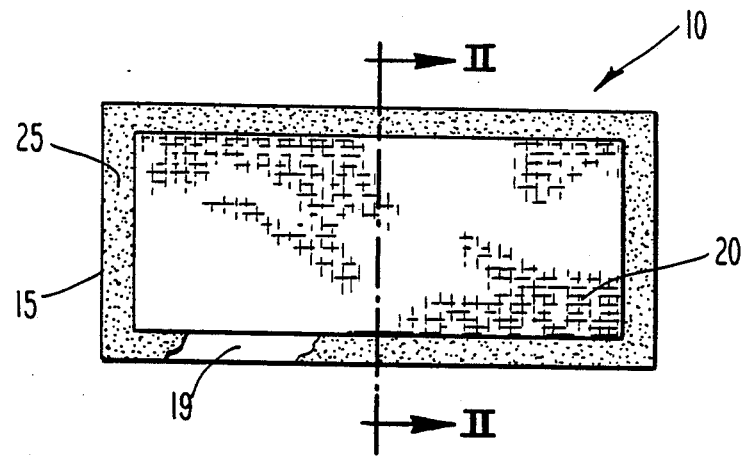
FIG. 1 is a plan view of a bandage of the present invention.

A bandage 10 according to the present invention is shown generally in plan view in FIG. 1. The bandage 10 includes a backing sheet 15 having a top face 17 (seen in FIG. 2) and bottom face 19 and is formed from a semi-interpenetrating polymer network material, a pressure sensitive adhesive layer 25 applied to the bottom face 19 and a section of gauze 20 which partially covers the bottom face 19 of the backing sheet 15. The bottom face 19 will be facing the application site (not shown) as the bandage is applied to the site. The top face 17 will face away from the application site.

Figure 2:
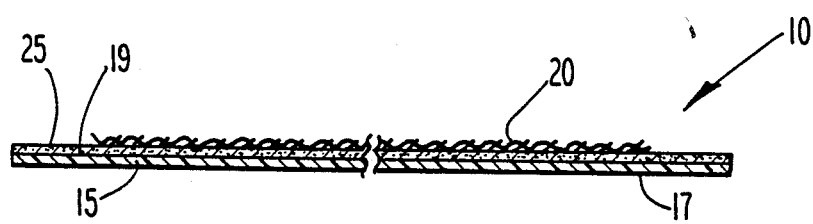
FIG. 2 is a section taken generally along line II—II of FIG. 1.

FIG. 2 illustrates a sectional view taken generally along line II—II of FIG. 1. The bandage 10 has a backing sheet 15 having a top face 17 and a bottom face 19. The pressure sensitive adhesive layer 25 covers the bottom face 19 of the bandage 10.

Figure 3:
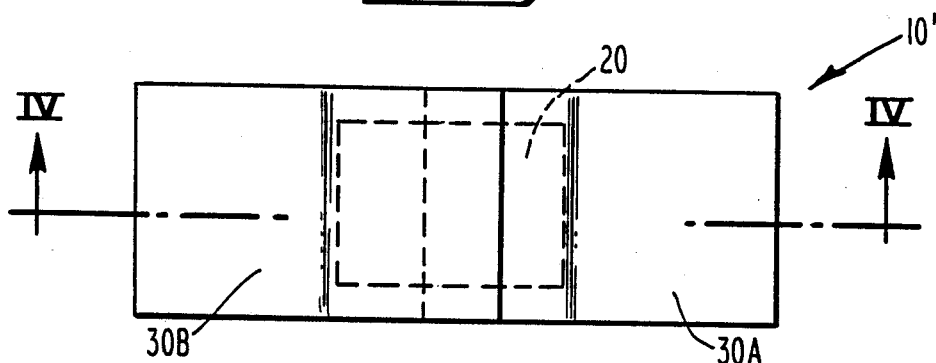
FIG. 3 is a plan view of another embodiment of the present invention.

FIG. 3 illustrates another embodiment of a bandage 10' according to the present invention. The bandage 10' includes gauze 20' (shown in phantom) covered by first and second backing sheets 30A and 30B.

Figure 4:
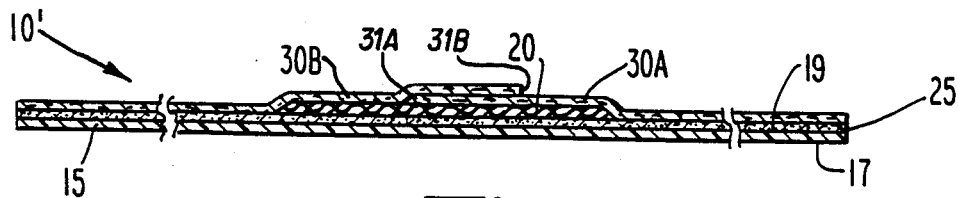
FIG. 4 is a section taken generally along line IV—IV of FIG. 3.

FIG. 4 shows the bandage 10' in greater detail. The second backing sheet 30B overlaps the first backing sheet 30A in such a manner as to allow for easy separation by grasping edge 31B of the second backing sheet 30B and pulling the edge 31B away from the bandage. The backing sheet 30A can then be removed in the same manner by grasping edge 31A and pulling backing sheet 30A away from the bandage. The bandage 10' can then be utilized with the gauze 20' overlaying the area or areas desired to be covered. The bandage 10' further includes backing material 15 with a top face 17 and the bottom face 19. A pressure sensitive adhesive layer 25 covers the face 19 of the bandage 10'.

The backing sheet can be waterproof up to 200 psi. The backing sheet can be transparent.

Figure 5:
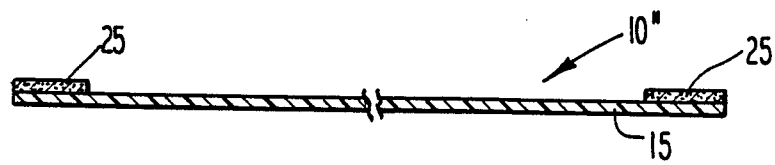
FIG. 5 is a sectional view of yet another embodiment of the present invention.

At FIG. 5 is shown a sectional view of a bandage 10" of another embodiment of the present invention. Pressure sensitive adhesive 25 is applied along the edges of backing material 15 which allows for the bandage 10" to be utilized as a wrap or support where no absorbent function is desired or necessary.

A bandage according to the present invention was prepared as follows:

A portion of medical grade polyorganosiloxane, Silastic ® (trademark of Dow Corning Corporation) MDX4-4210 was prepared by blending the base component with the catalyst component at a 10:1 ratio, as instructed by the manufacturer. The polyorganosiloxane was then mixed with kerosene (Fisher Scientific Company) in such proportions as to effect a 1:3 ratio of polyorganosiloxane to kerosene. The mixture was then applied to a substrate of expanded PTFE film, manufactured by Tetratec Corporation of Feasterville, PA, by means of a spray apparatus; thus creating an IPN upon curing of the thermoset as described in U.S. patent application Ser. No. 000,389. The IPN was determined to have a moisture vapor transmission rate of 628 grams per square meter per day, ASTM method E96-B66B, and a hydrostatic resistance of 70 psi measured according to Fed. Std. 191 Method 5512.

A pressure sensitive acrylic free film transfer adhesive commercially known as H-521 and supplied by Flexcon Company, Inc. of Spencer, MA was then applied to one surface of a 2.75"×1" piece of the IPN membrane. A 1"×¾" piece of STERI-PAD ® (trademark of Johnson & Johnson Company) absorbent gauze was then affixed in the center of the same surface of the membrane. The exposed adhesive was then covered with the protective release backing which was previously removed from the pressure sensitive free film transfer adhesive.

If desired, the bandage can be packaged and sterilized until use.

The above described configuration constitutes a transparent waterproof, yet breathable, bandage device. Other configurations of adhesives, absorbent gauze materials and other bandage shapes may be satisfactory for such bandage type applications. Preferred forms of the invention have been described and illustrated herein for purposes of illustration only and not for purposes of limitation, and various modifications or alternatives may suggest themselves to those skilled in the art, all of which are intended to be within the spirit and scope of the present invention as defined in the appended claims.

I claim:

1. A bandage comprising:
   a backing sheet comprising a gas permeable, water impermeable membrane which consists essentially of a semi-interpenetrating polymer network; and
   a fastening means whereby said bandage is affixed to an affected area to a patient.

2. A bandage as recited in claim 1 in which said semi-interpenetrating polymer network comprises fibrillated polytetrafluoroethylene and crosslinked polyorganosiloxane.

3. A bandage as recited in claim 1 in which said fastening means consists of a pressure sensitive adhesive.

4. A bandage as recited in claim 1 in which said backing sheet is waterproof up to 200 psi.

5. A bandage as recited in claim 1 in which said backing sheet is transparent.

6. A bandage as recited in claim 1 in which said backing sheet is translucent.

7. A bandage comprising:
   a backing sheet comprising a gas permeable water impermeable membrane which consists essentially of a semi-interpenetrating polymer network;
   a fastening means for affixing said bandage to an affected area of a patient; and
   an absorbent means for absorbing discharge from the affected area.

8. A bandage as recited in claim 7 in which said semi-interpenetrating polymer network comprises fibrillated polytetrafluoroethylene and crosslinked polyorganosiloxane.

9. A bandage as recited in claim 7 wherein said absorbant means consists of gauze.

10. A bandage as recited in claim 7 in which said fastening means consists of a pressure sensitive adhesive.

11. A bandage as recited in claim 7 in which said backing sheet is waterproof up to 200 psi.

12. A bandage as recited in claim 7 in which said backing sheet is transparent.

13. A bandage as recited in claim 7 in which said backing sheet is translucent.

* * * * *